Dec. 13, 1960 | O. O. DUNHAM | Plant Pat. 2,004
CHRYSANTHEMUM PLANT
Filed July 27, 1959
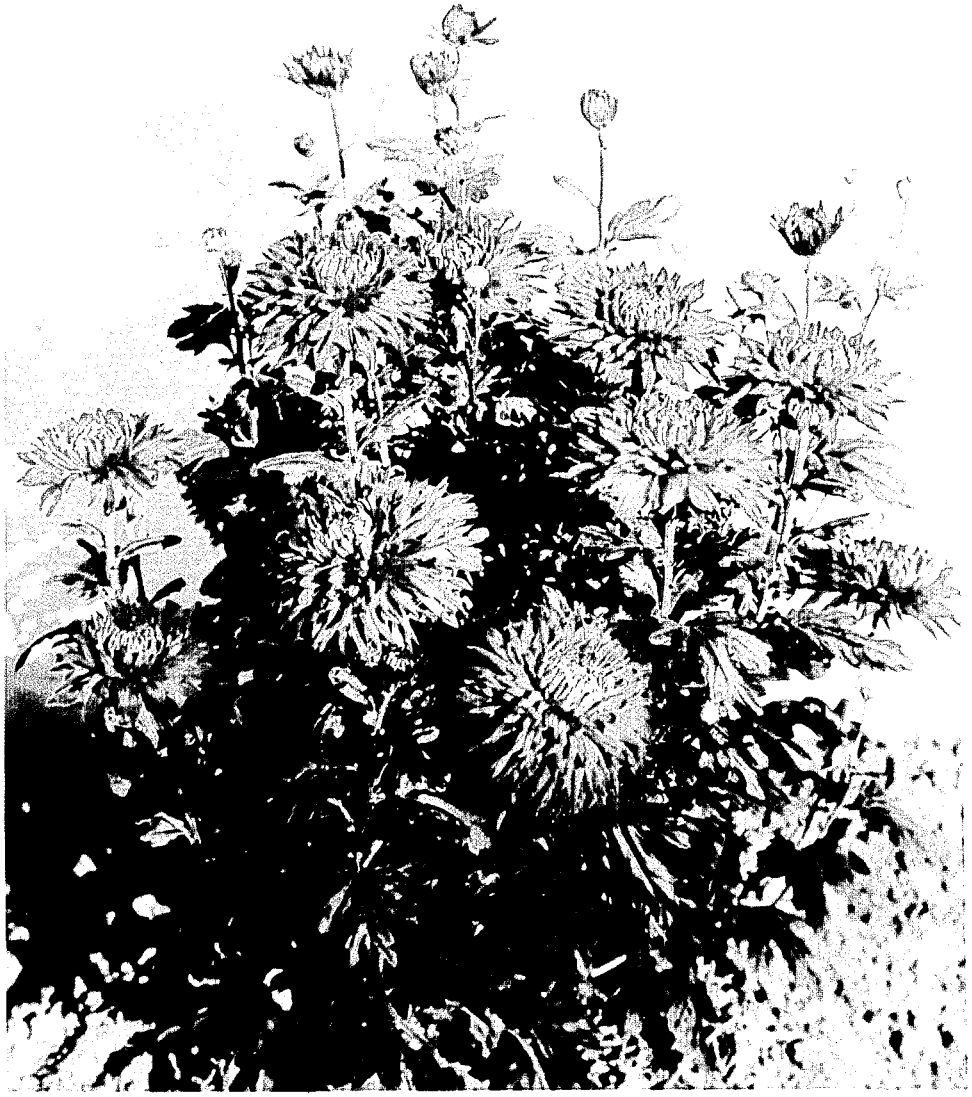
Inventor
O. O. Dunham
by Robb & Robb
attorneys United States Patent Office Plant Pat. 2,004
Patented Dec. 13, 1960

2,004

CHRYSANTHEMUM PLANT

Orville O. Dunham, Niles, Mich., assignor to George J. Ball, Inc., West Chicago, Ill., a corporation of Illinois Filed July 27, 1959, Ser. No. 829,946

1 Claim. (Cl. 47—60)

My present invention comprises a new and distinct variety of chrysanthemum plant, which seedling is the result of crossing the variety "Ablaze" (unpatented) which is a variety of my own introduction with the unpatented variety which I have designated as "No. 5350."

The object of this invention has been to produce a new variety of chrysanthemum of the indicum type which will have some of the color tendencies of the parent "Ablaze" but an improvement thereover with better plant habit than both of the parents, the parent "No. 5350" being a much lighter color than the parent "Ablaze."

This present new variety is one of the results of a program of development which I have been conducting for some period of time requiring the careful selection and cross-breeding of various plants, particularly basically of the so-called American garden chrysanthemum type, and the crossing of the same with the plants of the type of so-called English early chrysanthemums. The endeavor in conducting this program has been to take advantage of the continuous flowering features of the English early chrysanthemum with the early flowering feature of the American garden chrysanthemums and some of the better attributes of the latter.

The result of the specific hybridization previously referred to has been to produce my present new and distinct variety of chrysanthemum plant, characterized by the strong red to dark red color of its blooms, the very double arrangement of its petals, the large size of its blooms, its better habit and the early, continuous and long blooming period.

More specifically, the blooms of my new variety are of the strong red to dark red color (Nickerson Color Fan published by Munsell Color Company). As grown in the vicinity of Niles, Michigan, under uniform culture, the plants of my new variety have grown to an average height of fourteen to eighteen inches.

My new variety appears to have quite a number of characteristics of both of the parents but better characteristics than either separately and my new variety differs from both of its parents and from other known varieties in many respects.

In comparing the color of the bloom of my new variety with the color of the blooms of the variety "Ablaze," it is to be noted that the color of the latter is somewhat stronger red whereas the color of the blooms of my new variety is not quite as dark. The petal arrangement in my new variety is more reflexed and the blooms are more symmetrical than either parent with the blooms of my new variety being somewhat smaller in size than the parent "Ablaze." The petal arrangement of my new variety is very double and innumerable petals are found under normal conditions.

Under the conditions of culture previously mentioned, which have been undertaken in the region of Niles, Michigan, plants of my new variety have shown very vigorous growth, in somewhat more compact form with branching and slightly more dwarf in size than the parent "Ablaze."

My new variety when grown in the region of Niles, Michigan, blooms much earlier than the parent "Ablaze," which is the pollen parent, such blooming taking place from early September and lasting until a killing frost. The seed parent "No. 5350" is likewise of an early flowering type and therefore the instant variety takes its early blooming from the said seed parent.

One of the interesting aspects of my new variety is the fact that only a killing frost will cause the blooming to stop.

My new variety has been found to retain its distinctive characteristics through successive asexual reproduction.

My new variety has been asexually reproduced by cuttings, in the vicinity of Niles, Michigan.

The accompanying drawing forming a part hereof shows a typical plant of my new variety of chrysanthemum.

The following is a detailed description of my new variety of chrysanthemum plant, the color references being to the Nickerson Color Fan published by Munsell Color Company:

Parentage: Seedling.
- *Seed parent.*—No. 5350 (unpatented).
- *Pollen parent.*—"Ablaze" (unpatented).

Classification: Botanic—*Chrysanthemum indicum.*

*Flower*

Blooming Habit: Blooms profusely and continuously from early September until killing frost.

Bud:
- *Size.*—Large.
- *Form.*—Short with flat top. Not affected by hot or wet weather. Sepals of no consequence.
- *Color.*—When petals first begin to unfurl—5R 3/7 dark red washed with 5R 4/12 strong red. When half blown: inside of petals—7.5R 4/11 dark reddish orange washed with 7.5R 3/6 moderate reddish brown; reverse of petals—10YR 8/10 moderate orange yellow washed with 7.5R 4/11 dark reddish orange.
- *Peduncle.*—Very long.
- *Aspect.*—Rough.
- *Color.*—Medium green in color.
- *Strength.*—Stiff; erect.
- *Opening.*—Bud opens well; somewhat affected by adverse conditions.

Bloom:
- *Size.*—Large.
- *Average size when fully expanded.*—5 inches (disbudded).
- *Borne.*—In clusters; irregular.
- *Stems.*—Long; strong.
- *Form.*—When first open—flat. Permanence—retains its form to the end.
- *Petalage.*—Very double. Number of petals under normal conditions—innumerable.
- *Color.*—Center of flower—between 5R 4/12 and 5R 3/7 Munsell Hue 5R. Outer petals—between 5R 4/12 and 5R 3/7 Munsell Hue 5R. Base of petals (singlet)—between 5R 4/12 and 5R 3/7 Munsell Hue 5R. Inside of petals—between 5R 4/12 and 5R 3/7 Munsell Hue 5R. Reverse of petals—between 5R 4/12 and 5R 3/7 Munsell Hue 5R. General tonality from a distance—between 5R 4/12 and 5R 3/7 Munsell Hue 5R.
- *Discoloration.*—General tonality at end of: First week—retains same color. Second week—retains much the same color. Third week—retains much the same color.

Petals:
- *Texture.*—Thin. Affected by bleaching in hot weather. Affected by some fungus infection in wet weather.

*Appearance.*—Velvety inside; satiny outside.

*Form.*—Pointed.

*Arrangement.*—Imbricated.

*Persistence.*—Hang on and dry.

*Lastingness.*—On the plant—very long. As cut flower—long.

Genital organs:

*Stamens, anthers.*—Small; few. Color—brilliant yellow. Arrangement—regular around styles.

*Stamens, filaments.*—Short. Color—vivid yellow.

*Styles.*—Columnar.

*Stigmas.*—White in color.

*Ovaries.*—All enclosed in calyx.

Form: Bush.

Growth: Vigorous; dwarf; branching; compact.

Foliage:

*Size.*—Large.

*Quantity.*—Abundant.

*Color.*—New foliage: upper side—normal green; under side—light green. Old foliage: upper side—dark green; under side—dark green.

*Shape.*—Three lobed.

*Texture.*—Upper side—smooth. Under side—velvety. Ribs and veins—ordinary.

*Edge.*—Smooth.

*Leaf stem.*—Green in color. Under side—smooth.

*Stipules.*—Short.

*Disease resistant.*—Susceptible to mildew under certain conditions.

I claim:

A new and distinct variety of chrysanthemum plant substantially as herein disclosed, characterized as to novelty by the strong red to dark red color of its blooms, the very double arrangement of its petals, the larger size of its blooms, its better habit, and the early, continuous and long blooming period.

No references cited.